US006455588B1

(12) United States Patent
Scammell et al.

(10) Patent No.: US 6,455,588 B1
(45) Date of Patent: Sep. 24, 2002

(54) COMPOSITIONS INCLUDING MODAFINIL FOR TREATMENT OF EATING DISORDERS AND FOR APPETITE STIMULATION

(75) Inventors: Thomas E. Scammell, Wellesley, MA (US); Matthew S. Miller, Newtown, PA (US)

(73) Assignee: Cephalon, Inc., West Chester, PA (US)

( * ) Notice: Subject to any disclaimer, the term of this patent is extended or adjusted under 35 U.S.C. 154(b) by 12 days.

(21) Appl. No.: 09/640,824

(22) Filed: Aug. 17, 2000

Related U.S. Application Data

(60) Provisional application No. 60/150,071, filed on Aug. 20, 1999.

(51) Int. Cl.[7] .............................................. A61K 31/165
(52) U.S. Cl. ....................... 514/618; 424/464; 424/442; 424/438; 424/439
(58) Field of Search ........................ 514/618; 424/464, 424/442, 438, 439

(56) References Cited

U.S. PATENT DOCUMENTS

| 4,177,290 A | 12/1979 | Lafon |
| 4,927,855 A | 5/1990 | Lafon |
| 5,180,745 A | 1/1993 | Lafon |
| 5,618,845 A | 4/1997 | Grebow et al. |
| 5,719,168 A | 2/1998 | Laurent |
| 5,810,745 A | 9/1998 | Chaffringeon |

FOREIGN PATENT DOCUMENTS

| WO | WO 95/01171 | 1/1995 |
| WO | WO 95/01333 | 1/1995 |
| WO | WO99/25329 | 5/1999 |

OTHER PUBLICATIONS

Nicolaidis and Hilaire, *Brain Research Bulletin* 1993, 32, 87–90.

*Primary Examiner*—Frederick Krass
(74) *Attorney, Agent, or Firm*—Robert T. Hrubiec; Eric K. Voelk

(57) ABSTRACT

Modafinil is effective in improving symptoms of eating disorders or in stimulating appetite.

30 Claims, 1 Drawing Sheet

COMPOSITIONS INCLUDING MODAFINIL FOR TREATMENT OF EATING DISORDERS AND FOR APPETITE STIMULATION

This application claims benefit of U.S. Provisional Application Ser. No. 60/150,071, filed on Aug. 20, 1999.

BACKGROUND OF THE INVENTION

1. Field of the Invention

The present invention is related to the fields of neuropharmacological agents, including agents that are useful in the treatment of eating disorders and agents that stimulate appetite to produce weight gain in both human and animals in need thereof

2. Description of Related Art

Modafinil ($C_{15}H_{15}NO_2S$), 2-(benzhydrylsulfinyl) acetamide, or 2-[(diphenylmethyl) sulfinyl] acetamide, is a synthetic acetamide derivative with wake-promoting activity, the structure of which has been described in French Patent No. 78 05 510 and in U.S. Pat. No. 4,177,290. Modafinil was tested in combination with various agents including apomorphine, amphetamine, reserpine, oxotremorine, hypnotics, yohimbine, 5-hydroxytryptophan, monoamine oxidase inhibitor (I.M.A.O.), and in several behavioral conditions, as described in the cited patents. The conclusion from such tests is that modafinil presents a neuropsychopharmacological spectrum characterized by the presence of excitation with hyperactivity and hypermotility; and by the absence of stereotypy except in strong doses, and as potentiating the effects of apomorphine and amphetamine. A method of preparation of a racemic mixture is described in the '290 patent and a method of preparation of a levorotatory isomer is described in U.S. Pat. No. 4,927,855 (both incorporated herein by reference). The levorotatory isomer is reported to be useful for treatment of hypersomnia, depression, Alzheimer's disease and to have activity towards the symptoms of dementia and loss of memory, especially in the elderly.

Modafinil has also been described as an agent with activity in the central nervous system, and as a useful agent in the treatment of Parkinson's disease (U.S. Pat. No. 5,180,745); in the protection of cerebral tissue from ischemia (U.S. Pat. No. 5,391,576); in the treatment of urinary and fecal incontinence (U.S. Pat. No. 5,401,776); and in the treatment of sleep apneas of central origin (U.S. Pat. No. 5,612,378). U.S. Pat. No. 5,618,845 describes modafinil preparations of a defined particle size less than about 200 microns that is more potent and safer than preparations containing a substantial proportion of larger particles. Preparations of modafinil have not been described, however, for use in treating eating disorders, or as appetite stimulants.

The hypothalamus plays a central role in the integrated control of feeding and energy homeostasis. Two neuropeptides (orexin-A and orexin-B, also known as hypocretin -1 and -2) have been identified that are derived from a common precursor, preprohypocretin. These peptides are reported to be localized in neurons within and around the lateral and posterior hypothalamus in adult rat brain, and have been shown to bind to and activate G protein-coupled receptors (Sakurai et al., *Cell* 92:573–585, 1998), and are also reported to stimulate appetite and food consumption (Wolf, *Nutr. Rev.* 56: 172–173, 1998). Although the appetite stimulating neuropeptides may prove useful for stimulating appetite, and/or promoting weight gain in a variety of situations, such as eating disorders including anorexia nervosa, disease related weight loss, or even in agricultural applications such as promoting faster weight gain in weanling animals, it is difficult to administer peptides that are active in the brain and central nervous system by an oral route. There is still a need, therefore for an oral preparation for treatment of eating, disorders or for promotion of weight gain.

SUMMARY OF THE INVENTION

The present disclosure provides a novel use for modafinil in treatment of eating disorders and in stimulating appetite in humans suffering from an eating disorder, or who want or need to gain weight for athletic performance or for cosmetic reasons. The present disclosure also provides novel veterinary or agricultural uses for modafinil in stimulating appetite and increasing the rate of weight gain in animals, particularly young animals or weanlings, and more particularly young animals of species that are utilized for meat. Although the orexin peptides are described as appetite stimulants, modafinil offers certain advantages over those peptides in the compositions and methods disclosed because modafinil has been shown to be an effective oral treatment with activity in the brain and central nervous system. As such, modafinil is more convenient to administer than a peptide agent would be, which must often be injected in order to be effective.

As such, the present invention may be described in certain embodiments as a method of treating an eating disorder in a mammal comprising administering to said mammal an amount of a modafinil compound effective to stimulate the appetite of said mammal. The present invention may also be described in certain embodiments as a method of promoting weight gain in a mammal comprising administering to said mammal an amount of a modafinil compound effective to stimulate the appetite of said mammal.

An aspect of the present disclosure is also a method of increasing appetite in a mammal comprising administering to said mammal an amount of a modafinil compound effective to increase the appetite of said mammal. A further aspect of the present disclosure may also be described as a method of treating a mammal suffering from the symptoms of an eating disorder comprising administering to said mammal a pharmaceutical composition comprising a modafinil compound in an amount effective to stimulate orexin activity in the central nervous system of said mammal.

In certain preferred embodiments of the invention, a mammal or subject to receive a modafinil compound may be a human or an animal, and in particular animals such as a bovine, ovine, caprine, or porcine animal. Such animals are also described as cows, calves, pigs, sheep, or goats, and may include various exotic animals that are raised for agricultural uses, for showing or for hunting, for example. It is understood that the present methods would also be useful for enhancing appetite in pets, such as dogs and cats, for example.

In certain preferred embodiments, a modafinil compound as used in the practice of the disclosed compositions and methods is modafinil. As disclosed herein and as used in the compositions and methods of the present invention, a modafinil compound may include a racemic mixture, and may be in an acid form, such as a metabolic acid of modafinil or a benzhydrylsulfinylacetic acid, a sulfone form, a hydroxylated form, a conjugated form such as a modafinil compound conjugated to a protein, a polysaccharide, a glucuronide or a sulfate, or a polymorphic form, it may include compounds containing isosteric replacements of the phenyl groups of modafinl, and polymorphic species or analogs of modafinil, or derivatives of cogeners and prodrugs, particularly those preparations that stimulate activity in the TMN, or that activate orexin neurons in the central nervous system when administered to a mammal. Prodrugs are known in the art as compounds that are converted to the active agent (modafinil) in the body of a subject.

The compositions and methods disclosed herein are useful, in certain embodiments, in the treatment, stabilization, or prevention of eating disorders in mammals, or humans, for example, and in particular in the treatment of anorexia nervosa, binge eating disorder, bulimia nervosa, undernutrition or malnutrition due to infancy, pregnancy or lactation, old age, or chronic disease, or in wasting associated with various diseases such as AIDS or AIDS Related Complex, for example.

Effective dosages as described herein include, but are not limited to an amount from about 1 to about 400 mg, or from about 100 to about 400 mg, or about 200 mg per daily dose for an adult human, or an equivalent dose for a human child or an animal. It is well known in the pharmaceutical art to prescribe drugs based on the body weight of a subject and calculating doses for humans or animals based on the present disclosure is well within the skill of a practitioner in the art. In an alternate method of describing an effective dose, an effective amount may be described, in certain embodiments as an amount that is effective to achieve a serum level of modafinil of from about 0.05 to about 20 .g/ml, or from about 1 to about 20 .g/ml in an animal or a human.

Preferred formulations include compositions in which a modafinil compound is formulated for oral administration, or more preferably those inn which a modafinil compound is formulated as a tablet. Preferred tablets contain lactose, corn starch, magnesium silicate, croscarmellose sodium, povidone, magnesium stearate, or talc in any combination. It is also an aspect of the present disclosure that a modafinil compound may be incorporated into a food product or a liquid.

In certain aspects, the present disclosure includes pharmaceutical compositions in unit dose form, for use in treating an eating disorder in a subject susceptible to the development of or suffering from an eating disorder, which comprises:

an amount of a modafinil compound such that one or more unit doses thereof are effective to stabilize or improve the symptoms of an eating disorder in said subject upon periodic administration.

Also in certain aspects, the present disclosure includes veterinary compositions in unit dose form, for use in increasing appetite in an animal, which comprises:

an amount of a modafinil compound such that one or more unit doses thereof are effective to increase the appetite of an animal upon periodic administration.

An aspect of the present disclosure may also be described as a therapeutic package for dispensing to, or for use in dispensing to, a mammal being treated for an eating disorder, comprising:

(1) one or more unit doses, each such unit dose containing an amount of a modafinil compound such that said one or more unit doses thereof are effective to stabilize or improve a symptom of an eating disorder in said mammal upon periodic administration and the unit doses being administered periodically, and (2) a finished pharmaceutical container therefor, said container containing (a) said unit dose or unit doses and (b) labeling directing the use of said package in the treatment of said mammal.

Although the compositions and methods disclosed herein have been described in light of certain preferred embodiments, it is understood that the modafinil compounds described herein may be orally administered with an inert diluent or an assimilable edible carrier, for example. The compositions may also be enclosed in hard or soft shell gelatin capsule, compressed into tablets, or incorporated directly with the food of the diet. For oral therapeutic administration, the active compounds such as modafinil may be incorporated with excipients and used in the form of ingestible tablets, buccal tablets, troches, capsules, elixirs, suspensions, syrups, wafers, and the like, although tablets are the generally preferred method of administering, modafinil. Such compositions and preparations should contain at least 0.1% of active compound. The percentage of the compositions and preparations may, of course, be varied and may conveniently be between about 2 to about 60% of the weight of the unit.

The tablets, troches, pills, capsules and the like may also contain any of the following: a binder, as gum tragacanth, acacia, cornstarch, or gelatin, excipients, such as dicalcium phosphate, a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring, for example. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

In certain embodiments, the disclosed compositions may be formulated to be administered by use of a skin patch, or transdermal delivery system. The administration of the modafinil compositions described herein transdermally may be accomplished by any of a number of systems known in the art. Examples of systems that may be adapted for use with the compositions described herein include those systems of transdermal administration described in U.S. Pat. No. 4,816,252; U.S. Pat. No. 5,122,382; U.S. Pat. No. 5,198,223; U.S. Pat. No. 5,023,084; U.S. Pat. No. 4,906,169, U.S. Pat. No. 5,145,682; U.S. Pat. No. 4,624,665; U.S. Pat. No. 4,687,481; U.S. Pat. No. 4,834,978; and U.S. Pat. No. 4,810,499 (all incorporated herein by reference.

These methods typically include an adhesive matrix or drug reservoir system and may include a skin permeation enhancement agent such as ethanol, polyethylene glycol 200 dilaurate, isopropyl myristate, glycerol trioleate, linolenic acid saturated ethanol, glycerol monooleate, glycerol monolaurate, n-decyl alcohol, capric acid, and certain saturated and unsaturated fatty acids, and their esters, alcohols, monoglycerides, acetate, diethanolamides and N,N-dimethylamides (See for examples, U.S. Pat. No. 4,906,169).

BRIEF DESCRIPTION OF THE DRAWING

The following drawing forms part of the present specification and is included to further demonstrate certain aspects of the present invention. The invention may be better understood by reference to this drawing in combination with the detailed description of specific embodiments presented herein.

DETAILED DESCRIPTION

Figure 1:
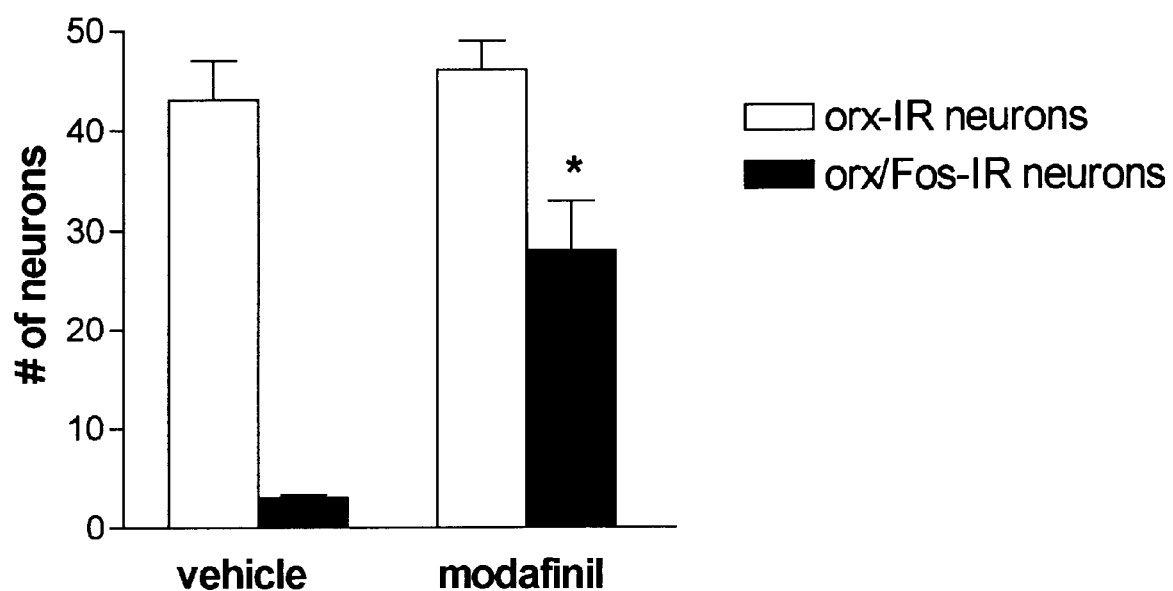
FIG. 1 depicts data orexin immunoreactive neurons (open bars) and orexin/fos immunoreactive neurons (shaded bars) in the perifornical regions of mice brains in mice treated with modafinil or vehicle.

Modafinil is an agent with activity in the central nervous system, and has been developed as a treatment for excessive daytime sleepiness associated with narcolepsy. The primary pharmacological activity of modafinil, like amphetamine-like agents, is to promote wakefulness. Modafinil promotes wakefulness in rats (Touret, et al., *Neuroscience Letters*, 189:43–46 (1995); Edgar and Seidel, *J. Pharmacol. Exp. Ther.*, 283:757–69 (1997)), cats (Lin et al., *Brain Research*, 591:3 19–326 (1992)), canines (Shelton et al., *Sleep* 18(10):817–826, (1995)) and non-human primates (DS-93-023, pp 180–181; Hernant et al., *Psychopharmacology*, 103:28–32 (1991)), as well as in models mimicking clinical situations, such as sleep apnea (English bulldog sleep disordered breathing model) (Panckeri et al, 1996) and narcolepsy (narcoleptic canine) (Shelton et al., *Sleep* 18(10):817–826, (1995)). Modafinil has also been demonstrated to be a useful agent in the treatment of Parkinson's disease (U.S. Pat. No. 5,180,745); in the protection of cerebral tissue from ischemia (U.S. Pat. No. 5,391,576); in the treatment of urinary and fecal incontinence (U.S. Pat. No. 5,401,776); and in the treatment of sleep apneas of central origin (U.S. Pat. No. 5,612,378). U.S. Pat. No. 5,618,845 describes modafinil preparations of a defined particle size less than about 200 microns that is more potent and safer than preparations containing a substantial proportion of larger particles.

Various neuroanatomical pathways have been investigated for their role in inducing and maintaining wakefulness, and some of the work has pointed to the potential role of the tuberomamillary nucleus (TMN) (Sherrin et al., *Science* 271:216–219, 1996). A study by Lin et al., (Proceedings of the National *Academy of Science, USA* 93:14128–14133, 1996) demonstrated selective activation of the anterior hypothalamus by modafinil, and the authors of that study also demonstrated that administration of modafinil to cats at a wake-promoting dose failed to cause activation of the TMN of the posterior hypothalamus. A similar study of wake-promoting doses of modafinil administered to rats (Engber et al., Neuroscience, 87:905–911 (1998)) also demonstrated that modafinil-induced wakefulness was not associated with activation of the TMN. Thus, while activation of the TMN has been implicated in normal wakefulness, the studies of these researchers has clearly taught that TMN activation was not involved in modafinil-induced wakefulness.

The present invention arises in part from the discovery that modafinil, when administered at wakefulness-promoting doses, does result in a stimulation of activity in the TMN of the posterior hypothalamus. Modafinil administration in rats reduced the activity of the neurons in the ventrolateropreoptic area (VLPO) of the hypothalamus, which are known to inhibit the activity of wake-promoting histaminergic neurons in the TMN during sleep. Activation of this histaminergic pathway by modafinil results in cortical activation and wakefulness. Thus, it appears that the physiologic basis for the wake-promoting actions of modafinil involves disinhibition of histaminergic neurons of the TMN by inhibitory actions on the VLPO. This represents the first pharmacologic agent known to produce wakefulness by activation of the TMN.

Furthermore, because the lateral hypothalamus is classically implicated in eating behavior, activation of this area by modafinil indicates that administration of modafinil will also be useful in control of eating disorders or for appetite enhancement. Because the present inventors also discovered that this area is innervated by orexin neurons, they were led to the discovery that modafinil is able to stimulate orexin activity in the hypothalamus and is thus useful as an agent in the treatment of eating disorders.

The present invention arose from studies in which double-immunostainini, techniques were used determine that orexin neurons projected directly onto the central nervous system nuclei known to be important in sleep-wakefulness regulation. The distribution of orexin-immunoreactive terminals was similar to that previously reported, including particularly dense innervation of the locus coeruleus, dorsal and median raphe nuclei, and tuberomammillary nucleus (Peyron et al., Neurosci. 18:9996–10015, 1998, Elias et al., *J. Comp. Neurol.* 402:442–459, 1998; Date et al., *Proc. Natl. Acad. Sci. USA*, 96:748–753, 1999). Innervation was also observed in the pedunculopontine nucleus, the lateral dorsal tegmental nucleus, the horizontal and vertical limbs of the diagonal band of Broca, and the medial septal nucleus, as previously reported (Peyron et al., *Neurosci.* 18:9996–10015, 1998; Nambu et al., *Brain Res.* 827:243–260, 1999). Double-label immunohistochemistry was performed in these sites in both rat and mouse brains. Histaminergic neurons in the tuberomammillary nucleus (adenosine deaminaseimmunoreactive) received very dense orexin innervation on cell bodies and on proximal dendrites. Noradrenergic neurons in the locus coeruleus received a similar dense innervation by orexin immunoreactive fibers. Somatic and dendritic appositions on tyrosine hydroxylase-immunoreactive cells were best observed on solitary neurons on the edges of the locus coeruleus. Serotonergic neurons in the dorsal and median raphe nucleus also were densely innervated. It was also observed that serotonergic neurons in the dorsal raphe are specifically targeted by orexin terminals. In the mouse brain, cholinergic neurons in the pedunculopontine nuclei, lateral dorsal tegmental nucleus, diagonal band, and medial septal nuclei, received orexin innervation. The innervation of cholinergic cells was particularly dense in the rat brain. In all sites, apparent somatic and dendritic appositions were observed in the chemically characterized neurons.

To determine that modafinil might act through orexin neurons, wild-type mice were injected at noon with modafinil (150 mg/kg i.p.), or vehicle, and sacrificed 2 hours later. Brains were removed, double immunostained for orexin and Fos (an indicator of neuronal activity), and cells were counted in the periforllical region. The number of orexin-immunoreactive neurons was the same in both groups (44–47 cells/section), but the modafinil-treated group had over three times as many Fos-immunoreactive neuronal nuclei (38 in the modafinil-treated mice vs. 11 in the vehicle controls; p=0.01). Within the population of orexin-immunoreactive neurons, modafinil induced a 9-fold increase in the number of Fos-immunoreactive cells (64% double labeled neurons in the modafinil group vs. 7% in the vehicle group, p=0.01) (FIG. 1). Thus, in the lateral hypothalamus, modafinil treatment is associated with activation of orexin neurons, and is thus useful as a treatment for eating disorders or for increasing appetite.

Modafinil also strongly activates orexin neurons in the lateral hypothalamus. However, it is difficult to conclude that modafinil promotes wakefulness solely through orexin neurons because it also induces neuronal activation in other brain regions implicated in sleep-wakefulness regulation, such as the suprachiasmatic nucleus, anterior hypothalamic area (Lin et al., *Proc. Natl. Acad. Sci. USA*, 93:14128–14133, 1996), tuberomammillary nucleus, and locus coeruleus. Since orexin neurons heavily innervate the tuberomammillary nucleus and locus coeruleus (Peyron et al., *Neurosci.* 18:9996–10015, 1998), it is possible that modafinil may activate the orexin system which then recruits other arousal regions.

Prior to any invention disclosed or claimed herein, modafinil was known in the art in the form of a therapeutic package, marketed under the name Provigil®. Provigil® is a pharmaceutical product manufactured by Cephalon, Inc. of West Chester. Pa. and is also marketed by Cephalon, Inc. Provigil® is supplied as tablets containing 100 mg or 200 mg modafinil. In commercial use, modafinil-containing therapeutic packages in the prior art were labeled and otherwise indicated for use in narcolepsy patients.

Accordingly, known in the prior art were therapeutic packages providing one or more unit doses of modafinil as an active ingredient thereof, supplied in a finished pharmaceutical container that contain said unit doses, and further contained or comprised labeling directing the use of said package in the treatment of a human disease or condition as described above. n the provided literature accompanying a pharmaceutical container are instructions that the daily dosage of modafinil is 200 mg/day given as a single dose in the morning. Although 400 mg/day was well tolerated in clinical trials, 200 mg/day is the optimum wakefulness promoting dose in adult humans.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of treating an eating disorder requiring appetite stimulation in a mammal comprising administering to a mammal in need thereof an amount of a modafinil compound effective to stimulate the appetite of said mammal.

2. A method of promoting weight gain in a mammal in need thereof comprising administering to said mammal an amount of a modafinil compound effective to stimulate the appetite of said mammal.

3. A method of increasing appetite in a mammal in need thereof comprising administering to said mammal an amount of a modafinil compound effective to increase the appetite of said mammal.

4. A method of treating a mammal suffering from the symptoms of an eating disorder requiring appetite stimulation comprising administering to said mammal a pharmaceutical composition comprising a modafinil compound in an amount effective to stimulate orexin activity in the central nervous system of said mammal.

5. The method of any of claims 1–4, wherein said modafinil compound is modafinil.

6. The method of any of claims 1–4, wherein said mammal is a human.

7. The method of claim 2 or 3, wherein said mammal is a domesticated animal useful for producing meat.

8. The method of claim 7, wherein said mammal is a bovine, ovine, caprine, or porcine animal.

9. The method of any of claims 1–4, wherein said mammal is human suffering from, or susceptible to an eating, disorder or to wasting associated with a disease.

10. The method of claim 9, wherein said eating disorder is anorexia nervosa.

11. The method of any of claims 1–4, wherein said effective amount is from about 1 to about 400 mg per daily dose.

12. The method of any of claims 1–4, wherein said effective amount is from about 100 to about 400 mg per daily dose.

13. The method of any of claims 1–4, wherein said effective amount is about 200 mg per daily dose.

14. The method of any of claims 1–4, wherein said effective amount is an amount that is effective to achieve a serim level of modafinil of from about 0.05 to about 20 g/ml in said mammal.

15. The method of any of claims 1–4, wherein said effective amount is an amount that is effective to achieve a serum level of modafinil of from about 1 to about 20 g/ml in said mammal.

16. The method of any of claims 1–4, wherein said modafinil compound is formulated for oral administration.

17. The method of any of claims 1–4, wherein said modafinil compound is formulated as a tablet.

18. The method of claim 17, wherein said tablet contains lactose, corn starch, magnesium silicate, croscarmellose sodium, povidone, magnesium stearate, or talc in any combination.

19. The method of any of claims 1–4, wherein said modafinil compound is incorporated into a food product or a liquid.

20. A therapeutic package for dispensing a modafinil compound to a mammal being treated for an eating disorder requiring appetite stimulation, comprising:
   (1) one or more unit doses, each unit dose containing a modafinil compound wherein that said one or more unit doses are effective to stabilize or improve a symptom of an eating disorder requiring appetite stimulation in said mammal upon periodic administration; and
   (2) a container therefor, said container containing said unit dose or unit doses and labeling directing the use of said package in the treatment of an eating disorder requiring appetite stimulation in said mammal.

21. The therapeutic package according to claim 20, wherein each unit dose is adapted for oral administration.

22. The therapeutic package according to claim 20, wherein the amount of the modafinil compound contained in each unit dose provides a dose effective to achieve a serum level of modafinil in said mammal of from about 0.05 to about 20 g/ml.

23. The therapeutic package according to claim 20, wherein the amount of the modafinil compound contained in each unit dose provides a dose effective to achieve a serum level of modafinil in said mammal of from about 1 to about 20 g/ml.

24. The therapeutic package according to claim 20, wherein the amount of the modafinil compound contained in each unit dose provides a dose effective to achieve a serum level of modafinil in said mammal of from about 1 to about 10 g/ml.

25. The therapeutic package according to claim 20, wherein the amount of the modafinil compound contained in each unit dose provides a dose effective to achieve a serum level of modafinil in said mammal of from about 0.5 to about 1.5 g/ml.

26. The therapeutic package according to claim 20, wherein each unit dose comprises a tablet for oral administration.

27. The therapeutic package according to claim 20, wherein said modafinil compound is modafinil.

28. The therapeutic package according to claim 20, wherein said mammal has or is susceptible to anorexia nervosa.

29. The therapeutic package according to claim 26, wherein said tablet comprises lactose, corn starch, magnesium silicate, croscarmellose sodium, povidone, magnesium stearate, or talc.

30. The therapeutic package according to claim 20, wherein said mammal is a human.

* * * * *